United States Patent [19]

Bröcker et al.

[11] Patent Number: 5,817,891

[45] Date of Patent: Oct. 6, 1998

[54] PREPARATION OF ALKYLPHENOLS

[75] Inventors: Franz Josef Bröcker; Peter Trübenbach, both of Ludwigshafen; Manfred Baumann, Mannheim; Jürgen Schubert, Dirmstein, all of Germany

[73] Assignee: BASF Aktiengesellschaft, Ludwigshafen, Germany

[21] Appl. No.: 715,830

[22] Filed: Sep. 19, 1996

[51] Int. Cl.$^6$ .................................................. C07C 37/07
[52] U.S. Cl. ........................................... 568/799; 502/333
[58] Field of Search ............................ 568/799; 502/333

[56] References Cited

U.S. PATENT DOCUMENTS

| | | | |
|---|---|---|---|
| 4,038,175 | 7/1977 | Bhasin et al. | 208/144 |
| 4,128,728 | 12/1978 | Arnold et al. | 568/799 |
| 4,538,009 | 8/1985 | Goetz et al. | 568/799 |
| 4,600,799 | 7/1986 | Broecker et al. | 568/799 |
| 4,929,762 | 5/1990 | Matsunaga et al. | 569/799 |
| 4,933,507 | 6/1990 | Inoki et al. | 569/799 |
| 4,940,687 | 7/1990 | Liu et al. | 502/333 |
| 5,378,767 | 1/1995 | Massie | 525/339 |

*Primary Examiner*—James H. Reamer
*Attorney, Agent, or Firm*—John H. Shurtleff

[57] ABSTRACT

A process for the preparation of alkylphenols of the formula I

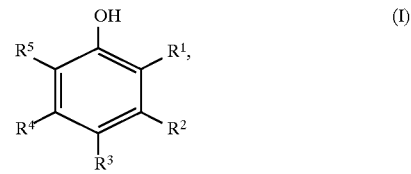

in which $R^1$, $R^2$, $R^3$, $R^4$, and $R^5$ stand for hydrogen or $C_1$–$C_8$ alkyl, by reaction of an alkylcyclohex-2-en-1-one of the formula II

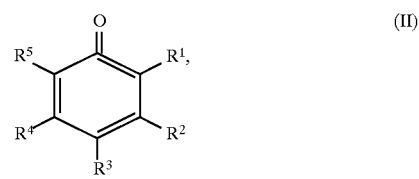

in which $R^1$, $R^2$, $R^3$, $R^4$, and $R^5$ have the aforementioned meanings, at temperatures of from 200° to 400° C. and pressures ranging from 0.01 to 50 bar in the presence of palladium-on-$\alpha$-$Al_2O_3$ catalysts, wherein the catalyst used has a specific surface area (BET) of from 1 to 10 m$^2$/g, a pore diameter of from 5 nm to 300 $\mu$m and a pore volume of from 0.1 to 0.5 cm$^3$/g, from 80 to 100% of the pores having a diameter of from 40 to 400 nm, and also novel palladium-on-$\alpha$-$Al_2O_3$ catalysts as obtained from a fine-grained alumina powder by steps of molding, pyrolysis and calcination.

9 Claims, No Drawings

PREPARATION OF ALKYLPHENOLS

The present invention relates to a process for the preparation of alkylphenols by catalytic dehydrogenation of alkylcyclohex-2-en-1-ones at elevated temperatures over palladium-on-α-Al$_2$O$_3$ catalysts, and in particular to the preparation of 2,3,6- trimethylphenol from 2,3,6-trimethylcyclohex-2-en-1-one.

DE-A 1,668,874 reveals the conversion of 2,3,6-trimethyl-2-cyclohexen-1-one by dehydrogenation over supported palladium catalysts. The supports described are aluminum oxide, silicic acid, or activated charcoals. For operation in the gas phase there is described only dehydrogenation over a Pd/SiO$_2$ catalyst.

If this dehydrogenation is carried out using the catalysts mentioned in a continuous plant, it is found that only briefly acceptable results are achieved, since the catalyst activity drops steeply after only a few hours. Thus it has not hitherto been possible to operate with these catalysts over relatively long periods.

It is thus an object of the present invention to overcome the aforementioned drawbacks and in particular to provide a dehydrogenation catalyst possessing at high yield and selectivity as long an on-stream time as possible without appreciable loss of activity and thus in this way providing an economical dehydrogenation process.

Accordingly, we have found a novel and improved process for the preparation of an alkylphenol of the general formula I

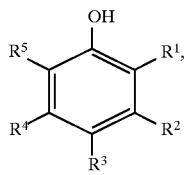

in which R$^1$, R$^2$, R$^3$, R$^4$, and R$^5$ stand for hydrogen or C$_1$–C$_8$ alkyl, by reaction of an alkylcyclohex-2-en-1-one of the general formula II

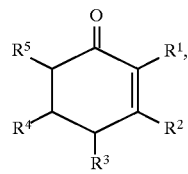

in which R$^1$, R$^2$, R$^3$, R$^4$, and R$^5$ have the aforementioned meanings, at temperatures of from 200° to 400° C. and pressures ranging from 0.01 to 50 bar in the presence of a palladium-on-α-Al$_2$O$_3$ catalyst, wherein the catalyst used has a specific surface area (BET) of from 1 to 10 m$^2$/g, a pore diameter of from 5 nm to 300 μm and a pore volume of from 0.1 to 0.5 cm3/g, from 80 to 100% of the pores having a diameter of from 40 to 400 nm, and also novel palladium-on-α-Al$_2$O$_3$ catalysts.

The process of the invention can be carried out as follows:

The alkylcyclohex-2-en-1-one II can be passed, preferably in the vaporous (gaseous) state, at temperatures of from 200° to 400° C., preferably from 250° to 350° C. and more preferably from 280° to 310° C. and pressures ranging from 0.01 to 50 bar, preferably from 0.1 to 5 bar and more preferably under standard pressure conditions (atmospheric pressure), preferably in the gas phase, over a specific palladium-on-α-Al$_2$O$_3$ catalyst. Advantageously, a foreign gas can be mixed in with the alkylcyclohex-2-en-1-one II in the vaporous state prior to commencement of the reaction, for example nitrogen, argon, steam, or hydrogen, preferably steam or hydrogen and more preferably hydrogen, use normally being made of a ratio by volume of foreign gas to vaporous alkylcyclohex-2-en-1-one II of from 0.01:1 to 100:1, preferably from 0.1:1 to 10:1 and more preferably from 0.7:1 to 1.5:1 (approximately 1:1). The residence times over the catalyst are usually from 0.5 to 50 seconds, preferably from 2 to 10 seconds.

The special palladium-on-α-Al$_2$O$_3$ catalysts of the invention have a specific surface area (BET) of from 1 to 10 m2/g, preferably from 4 to 8 m2/g, a pore diameter of from 5 nm to 300 μm, preferably from 10 nm to 100 μm and more preferably from 20 nm to 50 μm and a pore volume of from 0.1 to 0.5 cm3/g, preferably from 0.2 to 0.3 cm3/g, from 80 to 100%, preferably from 80 to 98% and more preferably from 80 to 95% of the pores having a diameter of from 40 to 400 nm.

The preparation of the palladium-on-α-Al$_2$O$_3$ catalysts of the invention may be carried out by making the α-Al$_2$O$_3$ support by thermal treatment of γ-Al$_2$O$_3$ powder at temperatures of from 800° to 1400° C. There is obtained, depending on the temperature of calcination, a α-Al$_2$O$_3$ ceramic powder having different surface areas (BET) and bi-modal pore volume distributions. The α-Al$_2$O$_3$ ceramic powder usually has an average particle size of from 0.3 to 1.5 μm, preferably from 0.5 to 1 μm. This powder is usually deagglomerated by means of a dispersing agent and worked in with an organic binder in mixing equipment, for example a kneader, extruder, or shearing roll extruder. Shaping may be carried out by compression molding or extrusion. In order to remove the binder system, the shaped product is usually pyrolyzed in air or under a blanket of inert gas at from 400° to 600° C. and calcined at temperatures of from 700° to 1200° C., preferably from 800° to 1000° C. Impregnation with a palladium salt solution, such as nitrate, nitrosylic nitrate, halide, carbonate, carboxylate, acetylacetonate, chlorine complexes, nitrite complexes, or amine complexes, preferably a palladium nitrate solution, and subsequent drying at 200° C. produces the dehydrogenation catalyst of the invention. The catalyst thus obtained can be filled into an adiabatic shaft reactor or a tubular reactor and activated by the passage of hydrogen at a space velocity of usually from 10 to 100 L(STP)/L$_{cat}$·h and heating to temperatures of from 200° to 400° C. This catalyst activation generally takes from 1 to 24 hours, preferably from 3 to 6 hours.

Examples of suitable dispersing agents are poly(ethylene glycol), poly(propylene glycol), poly(butanediol methylal), phthalate, poly(ethylene-co-vinyl acetate), montan ester wax, and stearic acid.

Examples of suitable organic binders are polyacetal, preferably polyoxymethylene, polyoxypropylene, polyethylene, polystyrene, poly(methyl methacrylate), poly-(ethylene oxide), ethylene vinyl acetate, or mixtures thereof.

The substituents R$^1$, R$^2$, R$^3$, R$^4$, and R$^5$ in the compounds I and II have the following meanings:

R$^1$, R$^2$, R$^3$, R$^4$, R$^5$ hydrogen or

C$_1$–C$_8$ alkyl, preferably C$_1$–C$_4$ alkyl such as methyl, ethyl, n-propyl, isopropyl, n-butyl, isobutyl, sec-butyl, and tert-butyl and more preferably methyl and ethyl.

Alkylphenols I, in particular 2,3,6-trimethylphenol, are suitable for use as intermediates for the synthesis of tocopherol (vitamin E), Karrer, P. et al, Helv. Chim. Acta 21,939, (1938), Ullmann (4th Edition), 23,643 et seq.

EXAMPLES

Example 1 a) Preparation of the catalyst support

To 1 kg of α-Al$_2$O$_3$ powder (CT 3000 SG, sold by Alcoa) having an average grain size of 0.7 μm there were added 162 g of polyacetal, a copolymer of trioxane and 2.5% of butanediol methylal, molar mass 150.000, 41 g of poly (butanediol methylal), molar mass 50.000, and also 50 g of poly(ethylene glycol), molar mass 800, and the mixture was kneaded at 180° C. over a period of 1 h. The coarse granulated material thus obtained was fed to a cylinder mill heated to 180° C. and equipped with 2 rolls and compressed to a "skin" having a thickness of from 2 to 3 $\mu$m, processed in a cutting mill to an ashlar-shaped granulated material and pyrolyzed in air in a rotary furnace at 900° C. over a period of 2 h.

The $\alpha$-$Al_2O_3$ support thus obtained possessed a specific surface area of 5.17 $m^2$/g, a pore diameter of from 5 nm to 300 $\mu$m and a pore volume of 0.225 $cm^3$/g. 83% of the pore diameters were in the range of from 40 to 400 nm.

b) Preparation of the palladium-on-$\alpha$-$Al_2O_3$ catalyst

In a coating drum, to 1 kg of the $\alpha$-aluminum oxide support obtained as described in Example 1a there was added a mixture of 18.18 g of palladium nitrate solution (11 wt% of Pd) and 210 g of water and the mixture was agitated until the solution had been taken up quantitatively. The impregnated material was dried over a period of 10 hours at 110° C. and then tempered over a period of 6 hours at 200° C.

c) Activation of the catalyst 100 mL of the catalyst prepared as described in Example 1b were filled into a tubular reactor having an internal diameter of 21 mm and treated with 10 liters of $H_2$/h. Over a period of 12 h, the reactor was heated to the reaction temperature of 300° C.

d) Preparation of 2,3,6-trimethylphenol

On reaching the reaction temperature, the amount of hydrogen was reduced to 4 L/h and gaseous 2,3,6-trimethylcyclohex-2-en-1-one was metered in via an evaporator. At the outlet of the reactor, the solid 2,3,6-trimethylphenol was separated in a yield and selectivity of 99.6% and analyzed. At a space velocity of 0.28 kg of 2,3,6-trimethylcyclohex-2-en-1-one/$L_{cat}$·h and a reaction temperature of 300° C., there was obtained a conversion of 100%.

Comparative Example A

Aluminum oxide support material (Norton T 484) having a specific surface area (BET) of 4.1 $m^2$/g and a pore volume of 0.406 $cm^3$ in a range of pore diameters of from 5 nm to 300 $\mu$m, in which 30% had pore diameters of from 40 to 400 nm, was impregnated with Pd nitrate solution as in Example 1b), so that a Pd catalyst containing 0.2 wt% of Pd was obtained.

100 mL of this catalyst were filled into a tubular reactor as described in Example 1c), activated and treated at 300° C. with 2,3,6-trimethyl-2-cyclohexen-1-one, in a manner similar to that described in Example 1d). At a space velocity of 0.280 kg/$L_{cat}$·h there was achieved, at a conversion of 100%, a yield and selectivity of 92%.

Comparative Example B 100 mL of an impregnated Pd catalyst prepared with an aluminum oxide support having a specific surface area (BET) of 0.98 $m^2$/g and a pore volume, in a range of pore diameters of from 5 nm to 300 mm, of 0.442 $cm^3$/g, which is quantitatively above a pore diameter of 400 nm, gave a conversion of 100% and a yield and selectivity of 83% for the dehydrogenation of 2,3,6-trimethyl-2-cyclohexen-1-one carried out in a manner similar to that described in Example 1d) at 300° C. and a space velocity of 0.280 kg/$L_{cat}$·h.

We claim:

1. A pallaidum-on-$\alpha$-$Al_2O_3$ catalyst having a specific surface area (BET) of from 1 to 10 $m^2$/g, a pore diameter of from 5 nm to 300 $\mu$m and a pore volume of from 0.1 to 0.5 $cm^3$/g, from 80 to 100% of the pores having a diameter of from 0.3 to 1.5 $\mu$m, a dispersing agent and a organic binder by the steps of molding, pyrolysis and calcination.

2. A process for the preparation of alkylphenols of the formula I

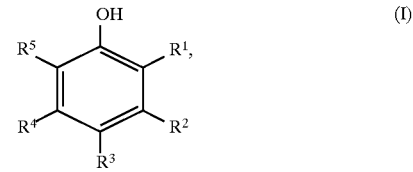

in which $R^1$, $R^2$, $R^3$, $R^4$, and $R^5$ stand for hydrogen or $C_1$–$C_8$ alkyl, by reacting an alkylcyclohex-2-en-1-one of the formula II

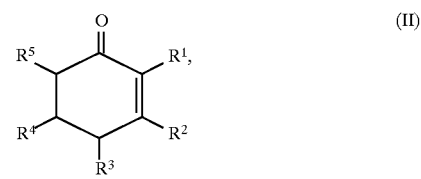

in which $R^1$, $R^2$, $R^3$, $R^4$, and $R^5$ have the aforementioned meanings, at temperatures of from 200° to 400° C. and pressures ranging from 0.01 to 50 bar in the presence of the catalyst defined by claim 1.

3. A process for the preparation of alkylphenols I as defined in claim 1, wherein the palladium-on-$\alpha$-$Al_2O_3$ catalyst used has a specific surface area (BET) of from 4 to 8 $m^2$/g.

4. A process for the preparation of alkylphenols I as defined in claim 1, wherein the reaction is carried out in the gas phase.

5. A process for the preparation of alkylphenols I as defined in claim 1, wherein the palladium-on-$\alpha$-$Al_2O_3$ catalyst used comprises a $\alpha$-$Al_2O_3$ support prepared from a $\alpha$-$Al_2O_3$ powder having a grain size of from 0.3 to 1.5 $\mu$m, a dispersing agent and an organic binder by molding, pyrolysis, and calcination.

6. A process for the preparation of alkylphenols I as defined in claim 1, wherein the palladium-on-$\alpha$-$Al_2O_3$ catalyst used comprises a $\alpha$-$Al_2O_3$ support prepared from a $\alpha$-$Al_2O_3$ powder having a grain size of from 0.5 to 1 $\mu$m, a dispersing agent and an organic binder by molding, pyrolysis, and calcination.

7. A process for the preparation of alkylphenols I as defined in claim 1, wherein the palladium-on-$\alpha$-$Al_2O_3$ catalyst used is prepared by impregnation of the $\alpha$-$Al_2O_3$ support with a palladium nitrate solution and drying at up to 200° C.

8. A process for the preparation of alkylphenols I as defined in claim 1, wherein the palladium-on-$\alpha$-$Al_2O_3$ catalysts are activated at from 250° to 330° C. with hydrogen.

9. A process for the preparation of alkylphenols I as defined in claim 1, wherein $R^1$, $R^2$, and $R^5$ stand for methyl and $R^3$ and $R^4$ for hydrogen.

* * * * *

UNITED STATES PATENT AND TRADEMARK OFFICE
CERTIFICATE OF CORRECTION

PATENT NO. : 5,817,891
DATED : October 6, 1998
INVENTOR(S) : Bröcker et al.

It is certified that error appears in the above-indentified patent and that said Letters Patent is hereby corrected as shown below:

IN THE CLAIMS:

Claim 1, line 8: after "from" and before "0.3", insert -- 40 to 400 nm, which is obtained from an $\alpha$-$Al_2O_3$ powder having a grain size of from --.

Signed and Sealed this

Second Day of March, 1999

Attest:

Q. TODD DICKINSON

*Attesting Officer*   Acting Commissioner of Patents and Trademarks